(12) United States Patent
Banju et al.

(10) Patent No.: US 8,777,843 B2
(45) Date of Patent: Jul. 15, 2014

(54) MULTI-BENDABLE MEDICAL DEVICE

(75) Inventors: Kazuo Banju, Hachioji (JP); Kimihiko Naito, Kawasaki (JP)

(73) Assignee: Olympus Medical Systems Corp., Tokyo (JP)

(*) Notice: Subject to any disclaimer, the term of this patent is extended or adjusted under 35 U.S.C. 154(b) by 69 days.

(21) Appl. No.: 13/222,730

(22) Filed: Aug. 31, 2011

(65) Prior Publication Data

US 2012/0071864 A1 Mar. 22, 2012

Related U.S. Application Data

(63) Continuation of application No. PCT/JP2010/068876, filed on Oct. 25, 2010.

(30) Foreign Application Priority Data

Mar. 8, 2010 (JP) ................................. 2010-050997

(51) Int. Cl.
*A61B 1/008* (2006.01)
(52) U.S. Cl.
USPC .............................................. 600/141; 606/1
(58) Field of Classification Search
USPC .................. 600/114, 137, 141, 142, 146, 149; 606/1
See application file for complete search history.

(56) References Cited

U.S. PATENT DOCUMENTS

| | | | |
|---|---|---|---|
| 5,174,277 A | 12/1992 | Matsumaru | |
| 6,454,703 B1 | 9/2002 | Ide | |
| 6,817,974 B2 * | 11/2004 | Cooper et al. | 600/142 |
| 2002/0058858 A1 | 5/2002 | Ogura et al. | |
| 2003/0036748 A1 | 2/2003 | Cooper et al. | |

FOREIGN PATENT DOCUMENTS

| | | |
|---|---|---|
| CN | 101528111 A | 9/2009 |
| CN | 101610710 A | 12/2009 |
| CN | 101610724 A | 12/2009 |
| DE | 10 2004 010 193 A1 | 9/2004 |
| EP | 2 130 478 A1 | 12/2009 |
| JP | A-62-281918 | 12/1987 |

(Continued)

OTHER PUBLICATIONS

International Search Report issued in International Application No. PCT/JP2010/068876 on Dec. 7, 2010 (with translation).

(Continued)

*Primary Examiner* — Aaron Roane
(74) *Attorney, Agent, or Firm* — Oliff PLC

(57) ABSTRACT

A medical device for multiple bends, includes a distal-side traction member which is inserted through the distal-side bending portion and the proximal-side bending portion, which is configured to bend the distal-side bending portion in the bending orientation, and which includes a distal-side fixing portion fixed to the distal end of the distal-side bending portion in the axial direction, and a proximal-side traction member which is inserted through the proximal-side bending portion, which is configured to bend the proximal-side bending portion in the bending orientation, and which includes a proximal-side fixing portion fixed to the distal end of the proximal-side bending portion in the axial direction. The proximal-side fixing portion is disposed at substantially the same position as the distal-side fixing portion in a circumferential direction.

4 Claims, 12 Drawing Sheets

(56) References Cited

FOREIGN PATENT DOCUMENTS

| JP | A-63-217316 | 9/1988 |
| JP | A-3-218723 | 9/1991 |
| JP | A-2001-95752 | 4/2001 |
| JP | A-2002-102152 | 4/2002 |
| JP | A-2002-177200 | 6/2002 |
| JP | A-2008-237811 | 10/2008 |

OTHER PUBLICATIONS

Sep. 20, 2012 Search Report issued in European Application No. 10847485.9.

Mar. 28, 2014 Office Action issued in Chinese Patent Application No. 201080063132.9 (w/English Translation).

* cited by examiner

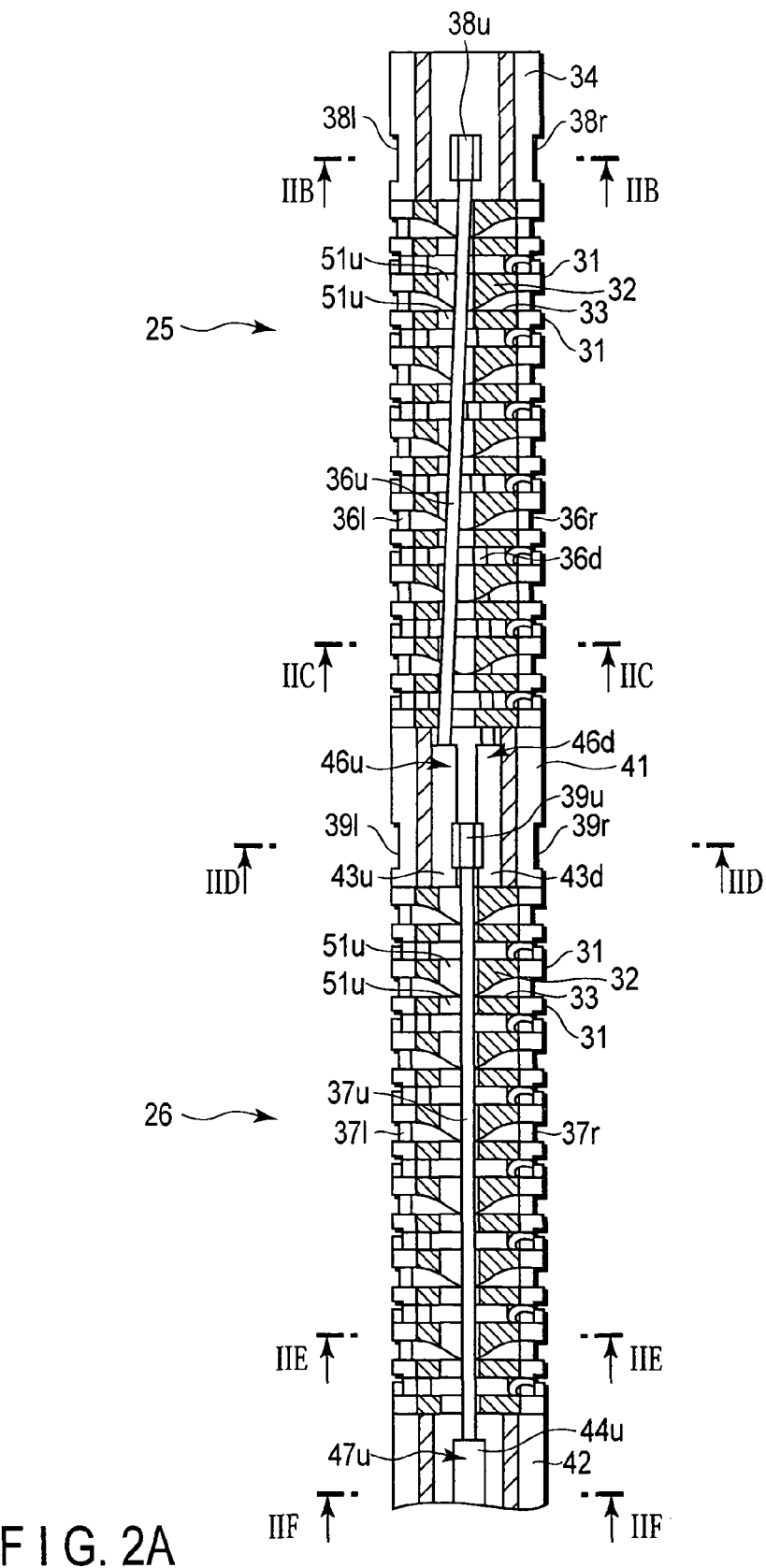
F I G. 2A

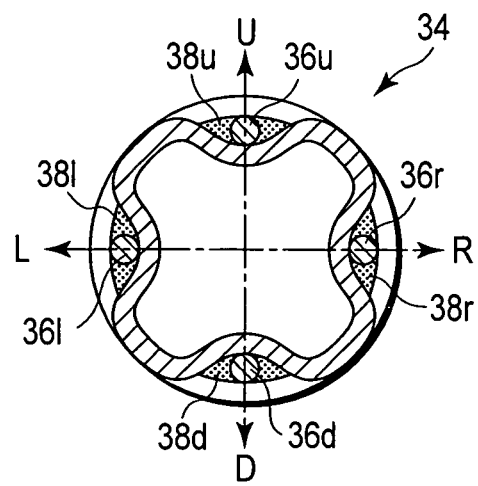
F I G. 2B
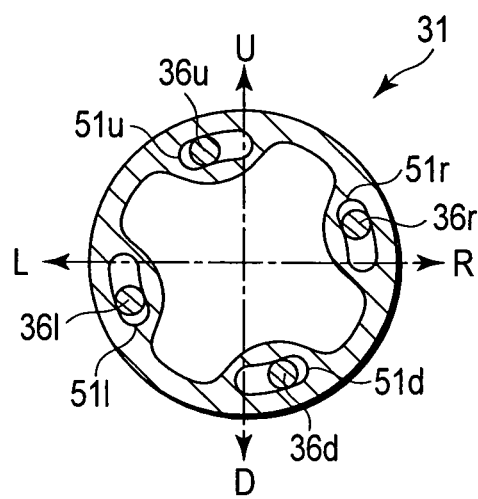
F I G. 2C

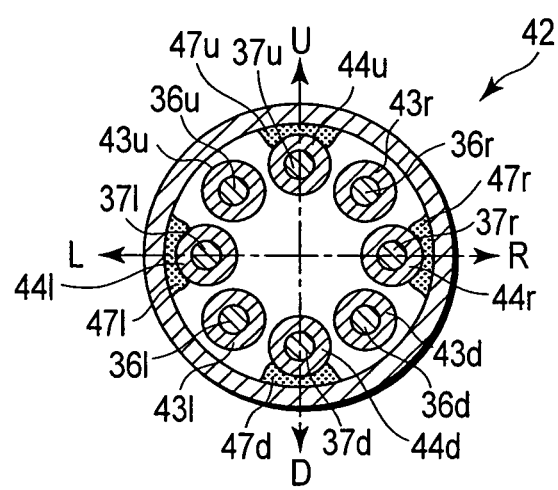
F I G. 2F

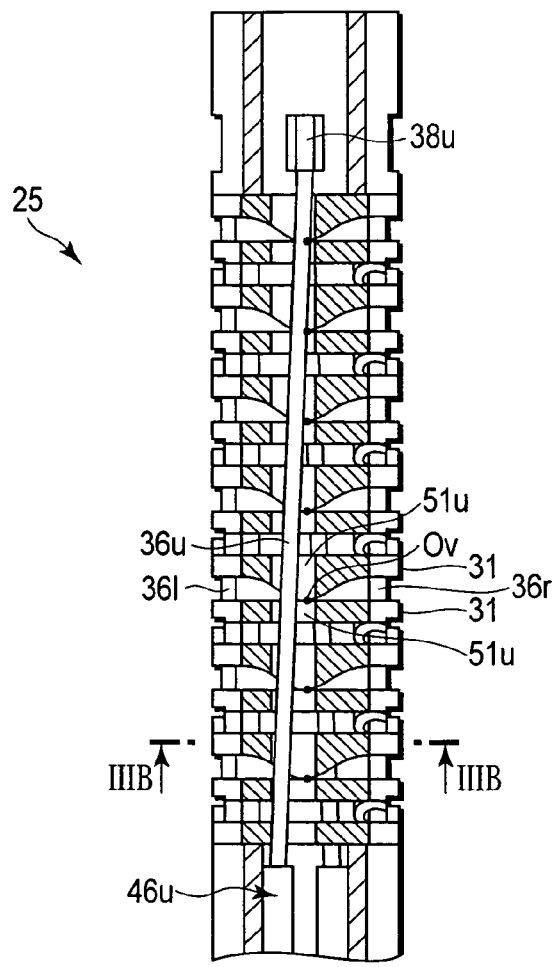
F I G. 3A
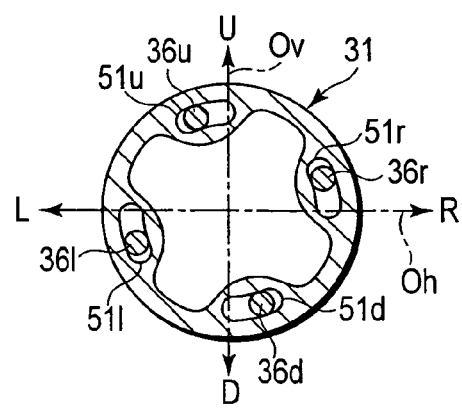
F I G. 3B

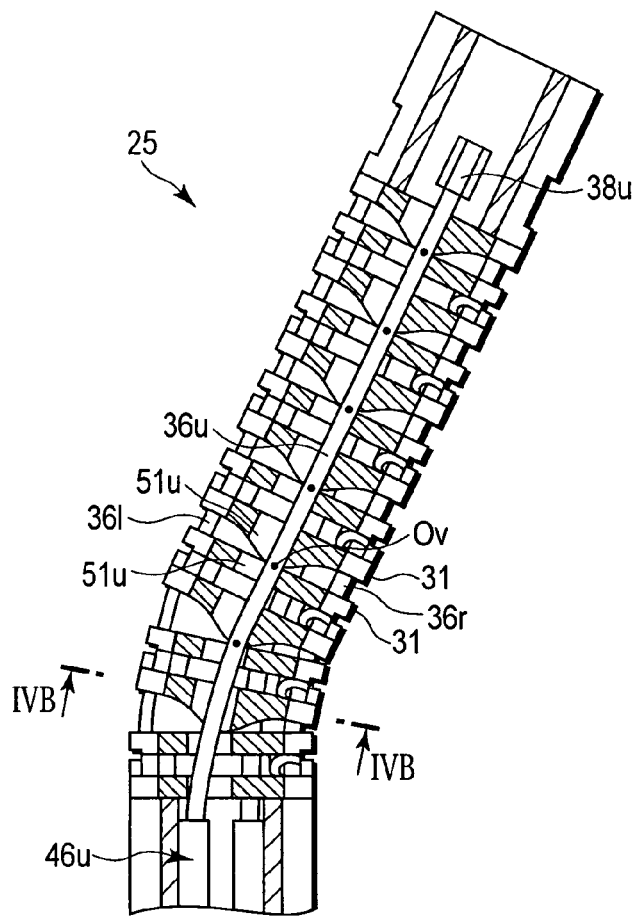
F I G. 4A
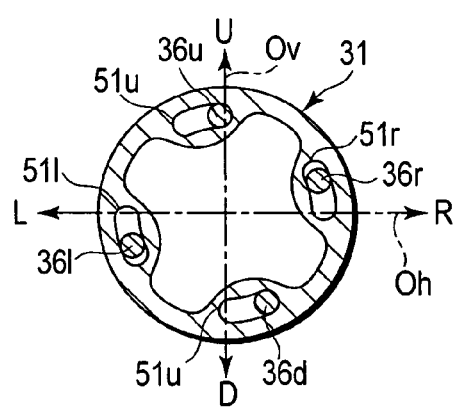
F I G. 4B

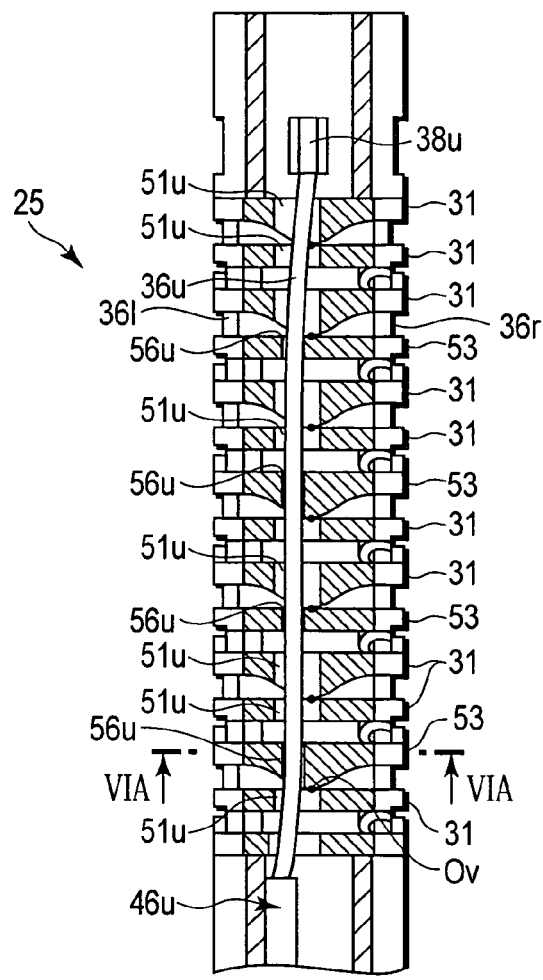
F I G. 6A
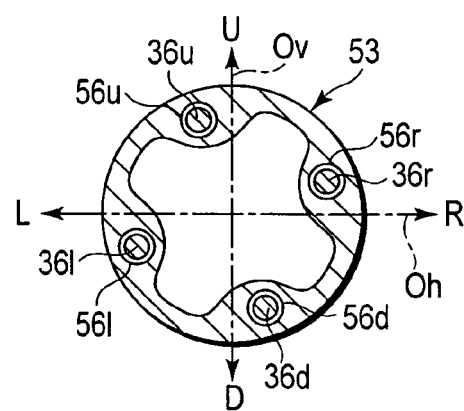
F I G. 6B

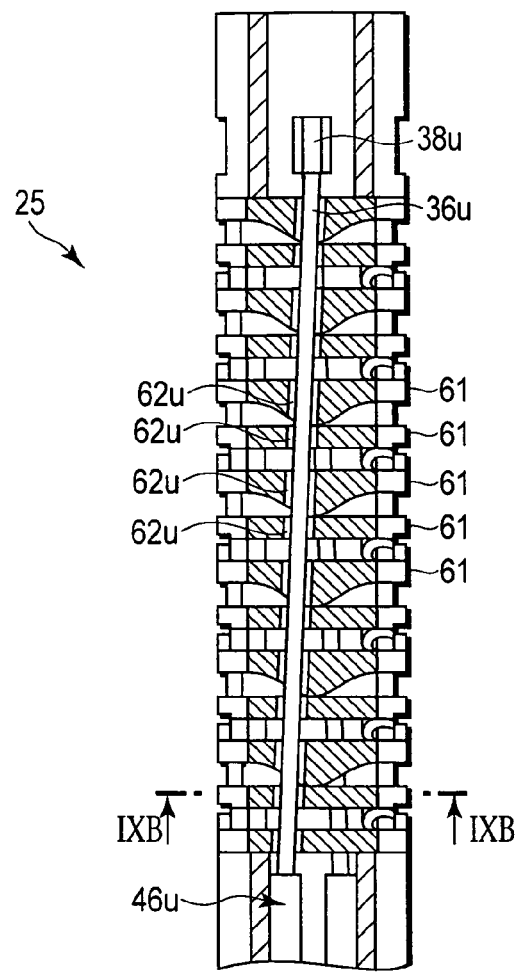
F I G. 9A
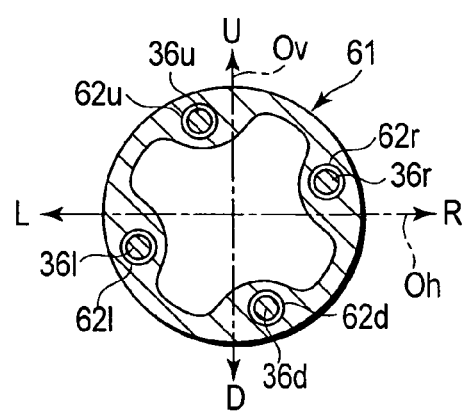
F I G. 9B

MULTI-BENDABLE MEDICAL DEVICE

CROSS REFERENCE TO RELATED APPLICATIONS

This application is a Continuation Application of PCT Application No. PCT/JP2010/068876, filed Oct. 25, 2010 and based upon and claiming the benefit of priority from prior Japanese Patent Application No. 2010-050997, filed Mar. 8, 2010, the entire contents of all of which are incorporated herein by reference.

BACKGROUND OF THE INVENTION

1. Field of the Invention

The present invention relates to a multi-bendable medical device in which a plurality of bending portions for bending operation are disposed in an insertion portion for insertion into a body.

2. Description of the Related Art

In Jpn. Pat. Appln. KOKAI Publication No. 2002-177200, an endoscope with two bends is disclosed. The endoscope with the two bends has an elongated insertion portion for insertion into a body. The insertion portion includes distal-side and proximal-side bending portions to be bent in vertical and horizontal directions in the distal end of the insertion portion. In a bending tube of each bending portion, many cylindrical bending pieces are axially coaxially arranged, and are rotationally connected to each other. The bending pieces adjoining to a predetermined bending piece on the distal and proximal sides are rotatable in the vertical direction and the horizontal direction, and the bending tube can be bent as a whole in an optional direction of the vertical and horizontal directions. At upper, lower, left and right positions in an internal peripheral portion of the bending piece, wire receiving portions are disposed. Through the wire receiving portions at the upper, lower, left and right positions, traction wires for bending motions in vertical and horizontal directions are passed, respectively. The distal ends of the traction wires are fixed to the distal end of the bending portion. The traction wires are passed through the insertion portion and introduced into an operation portion connected to the proximal end of the insertion portion. The traction of the traction wires for the bending motions in the vertical and horizontal directions makes it possible to bend the bending portion in the vertical and horizontal directions.

BRIEF SUMMARY OF THE INVENTION

According to one aspect of the present invention, there is provided a medical device for multiple bends includes an insertion portion which is configured to be inserted into a body and which includes a central axis and is configured to extend in an axial direction of the central axis, wherein:

the insertion portion includes:

a distal-side bending portion configured to bend in a bending orientation which is substantially orthogonal to the central axis, a proximal-side bending portion which is disposed closer to a proximal side than the distal-side bending portion in the axial direction and which is configured to bend in the bending orientation, a distal-side traction member which is inserted through the distal-side bending portion and the proximal-side bending portion and which is disposed on the side of the bending orientation, the distal-side traction member including a distal-side fixing portion fixed to the distal end of the distal-side bending portion in the axial direction, the distal-side traction member being pulled toward the proximal end in the axial direction to allow the distal-side bending portion to bend in the bending orientation, a proximal-side traction member which is inserted through the proximal-side bending portion and which is disposed on the side of the bending orientation, the proximal-side traction member including a proximal-side fixing portion fixed to the distal end of the proximal-side bending portion in the axial direction, the proximal-side traction member being pulled toward the proximal end in the axial direction to allow the proximal-side bending portion to bend in the bending orientation, and a holding portion which is provided at the distal end of the proximal-side bending portion in the axial direction and which is disposed on the side of the bending orientation and which is configured to hold the distal-side traction member movably back and forth in the axial direction, and the proximal-side fixing portion is disposed at substantially the same position as the distal-side fixing portion in a circumferential direction of the central axis, the holding portion is disposed at a position different from the proximal-side fixing portion in the circumferential direction, the distal-side bending portion includes two or more substantially cylindrical bending members which are substantially coaxially arranged in the axial direction and which are rotatably connected to each other, the two or more bending members include at least one through bending member, the through bending member includes a through portion, the through portion being disposed on the side of the bending orientation, extending in the axial direction, and supporting the distal-side traction member, the distal-side traction member being inserted through the through portion movably back and forth in the axial direction, and the through portion extends fully between the position of the distal-side fixing portion and the position of the holding portion in the circumferential direction.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a partial longitudinal sectional top view showing a bending part according to the first embodiment of the present invention;

FIG. 2B is a cross-sectional view showing the distal end of a distal-side bending portion according to the first embodiment of the present invention along the line IIB-IIB of FIG. 2A;

FIG. 2C is a cross-sectional view showing an intermediate portion of the distal-side bending portion according to the first embodiment of the present invention along the line IIC-IIC of FIG. 2A;

FIG. 2F is a cross-sectional view showing the proximal end of the proximal-side bending portion according to the first embodiment of the present invention along the line IIF-IIF of FIG. 2A;

FIG. 3A is a partial longitudinal sectional top view showing the distal-side bending portion according to the first embodiment of the present invention in a neutral condition;

FIG. 3B is a cross-sectional view showing the distal-side bending portion according to the first embodiment of the present invention in the neutral condition along the line IIIB-IIIB of FIG. 3A;

FIG. 4A is a partial longitudinal sectional top view showing the distal-side bending portion according to the first embodiment of the present invention in a rightward bent condition;

FIG. 4B is a cross-sectional view showing the distal-side bending portion according to the first embodiment of the present invention in the rightward bent condition along the line IVB-IVB of FIG. 4A;

FIG. 6A is a partial longitudinal sectional top view showing a distal-side bending portion according to a second embodiment of the present invention in a neutral condition;

FIG. 6B is a cross-sectional view showing the distal-side bending portion according to the second embodiment of the present invention in the neutral condition along the line VIB-VIB of FIG. 6A;

FIG. 9A is a partial longitudinal sectional top view showing a distal-side bending portion according to a third embodiment of the present invention; and FIG. 9B is a cross-sectional view showing the distal-side bending portion according to the third embodiment of the present invention along the line IXB-IXB of FIG. 9A.

DETAILED DESCRIPTION OF THE INVENTION

Embodiments of the present invention will be described with reference to the drawings.

A first embodiment of the present invention is described with reference to FIG. 1 to FIG. 2F.

Figure 1:
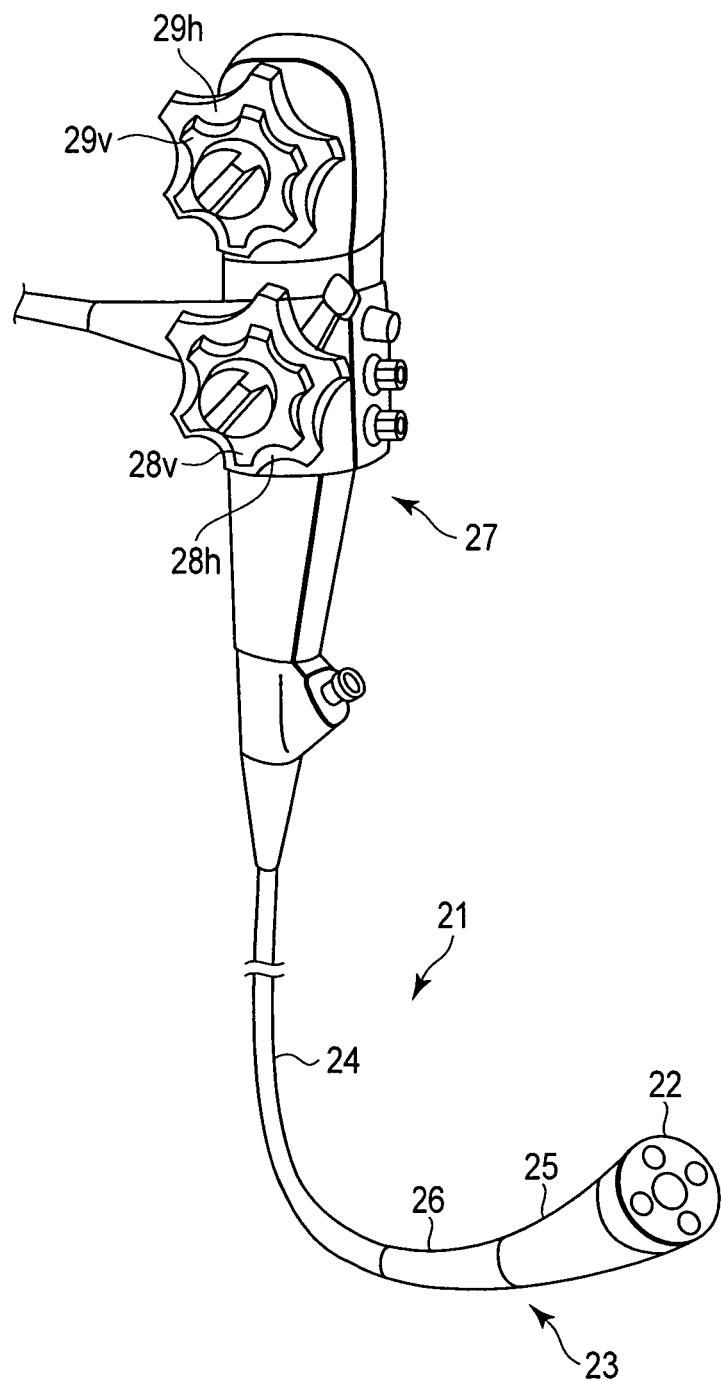
FIG. 1 is a perspective view showing an endoscope for two bends according to a first embodiment of the present invention.

Referring to FIG. 1, an endoscope for bi-bends includes an elongated insertion portion 21 for insertion into a body. The insertion portion 21 includes a hard tip portion 22 with rigidity, a bending part 23 for bending motion and an elongated flexible tube 24 with flexibility, and the hard tip portion 22, the bending part 23 and the flexible tube 24 are continuously provided from a distal side to a proximal side of the insertion portion 21. The bending part 23 includes distal-side bending portion 25 and proximal-side bending portion 26. The distal-side and proximal-side bending portions 25 and 26 can be bent in a vertical direction that is orthogonal to the central axis of the insertion portion 21, and in a horizontal direction that is orthogonal to the central axis and the vertical direction. The above vertical direction is composed of an upward orientation U and a downward orientation D mutually reversed, and the above horizontal direction is composed of a leftward orientation L and a rightward orientation R mutually reversed. The proximal end of the insertion portion 21 is connected with an operation portion 27 which is held and operated by an operator. The operation portion 27 includes a distal-side vertical bending operation knob 28$v$ which bends the distal-side bending portion 25 in the vertical direction, and a distal-side horizontal bending operation knob 28$h$ which bends the distal-side bending portion 25 in the horizontal direction. Furthermore, the operating portion 27 includes a proximal-side vertical bending operation knob 29$v$ which bends the proximal-side bending portion 26 in the vertical direction, and a horizontal bending operation knob 29$h$ which bends the proximal-side bending portion 26 in the horizontal direction.

The bending part 23 according to the present invention is described in detail with reference to FIG. 2A to FIG. 2F.

Referring to FIG. 2A, bending tubes of the bending portions 25 and 26 include many substantially annular bending pieces as bending members which are axially coaxially arranged, and which are rotationally connected to each other. In the present embodiment, through pieces 31 as through bending members are used as many bending pieces. The through pieces 31 are integrally formed by, for example, cutting or injection molding. The through piece 31 includes an annular main body and a pair of rotation portions 32 which are formed in a circular surface at one end of the annular main body. The pair of rotation portions 32 project in the axial direction, assume a smooth arc-like outer shape when diametrically viewed, and are disposed symmetrically to each other with respect to a central axis. A circular surface at the other end of the main body serves as a rotation support surface 33. The pair of rotation portions 32 of the other of the adjoining through pieces 31 are in contact with the rotation support surface 33 of one through piece 31. The other through piece 31 can rotate, with respect to one through piece 31, on the tops of the pair of rotation portions 32 around a rotation axis that passes the tops of the pair of rotation portions 32 and that is orthogonal to the central axis. Many pairs of rotation portions 32 of many through pieces 31 arranged in the axial direction are alternately disposed exactly at the top, bottom, left, and right. Many rotation axes are alternately disposed in the vertical and horizontal directions. The bending tubes can be bent as a whole in an optional direction of the vertical and horizontal directions.

Distal-side traction wires 36$u$, 36$d$, 36$l$ and 36$r$ as distal-side traction members are inserted through the distal-side bending portion 25 and the proximal-side bending portion 26. Proximal-side traction wires 37$u$, 37$d$, 37$l$ and 37$r$ as proximal-side traction members are inserted through the proximal-side bending portion 26.

Referring to FIG. 2A and FIG. 2B, a cylindrical distal fixing member 34 is coaxially connected to the most distal through piece 31 of the distal-side bending portion 25. The distal ends of the distal-side traction wires 36$u$ to 36$r$ are fixed to the internal peripheral surface of the distal fixing member 34, and distal-side wire fixing portions 38$u$, 38$d$, 38$l$ and 38$r$ are formed by the distal ends of the distal-side traction wires 36$u$, 36$d$, 36$l$ and 36$r$. The distal-side wire fixing portions 38$u$ to 38$r$ of the distal-side traction wires 36$u$ to 36$r$ for vertical and horizontal bending motions are disposed exactly at the top, bottom, left, and right, respectively.

Figure 2D:
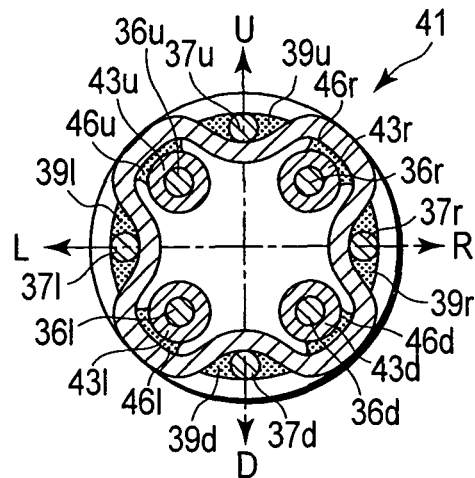
FIG. 2D is a cross-sectional view showing a connection portion of the distal-side and proximal-side bending portions according to the first embodiment of the present invention along the line IID-IID of FIG. 2A.

Referring to FIG. 2A and FIG. 2D, the most proximal through piece 31 of the distal-side bending portion 25 is coaxially connected to the most distal through piece 31 of the proximal-side bending portion 26 by a cylindrical distal-side connecting member 41. The distal ends of the proximal-side traction wires 37$u$ to 37$r$ are fixed to the internal peripheral surface of the distal-side connecting member 41, and proximal-side wire fixing portions 39$u$, 39$d$, 39$l$ and 39$r$ are formed by the distal ends of the proximal-side traction wires 37$u$, 37$d$, 37$l$ and 37$r$. The proximal-side wire fixing portions 39$u$ to 39$r$ are disposed at the same positions in the circumferential direction as the distal-side wire fixing portions 38$u$ to 38$r$, respectively. That is, the proximal-side wire fixing portions 39$u$ to 39$r$ for vertical and horizontal bending motions are disposed exactly at the top, bottom, left, and right in the circumferential direction, respectively.

In the proximal-side bending portion 26, the distal-side traction wires 36$u$, 36$d$, 36$l$ and 36$r$ are inserted axially movably back and forth through distal-side coil sheaths 43$u$, 43$d$, 43$l$ and 43$r$. The distal ends of the distal-side coil sheaths 43$u$, 43$d$, 43$l$ and 43$r$ are fixed to the internal peripheral surface of the distal-side connecting member 41, and form distal-side sheath fixing portions 46$u$, 46$d$, 46$l$ and 46$r$ as holding portions. The distal-side sheath fixing portions 46$u$ to 46$r$ are disposed at circumferential positions slightly different from the proximal-side wire fixing portions 39$u$ to 39$r$ in one orientation in the circumferential direction, respectively. In other words, the distal-side sheath fixing portions 46$u$ to 46$r$ are disposed at circumferential positions slightly different from the distal-side wire fixing portions 38$u$ to 38$r$ in one orientation in the circumferential direction, respectively. That is, the distal-side sheath fixing portions 46$u$ to 46$r$ for vertical and horizontal bending motions are circumferentially disposed on the left side of the top in the circumferential direction, on the right side of the bottom in the circumferential direction, on the lower side of the left in the circumferential direction, and on the upper side of the right in the circumferential direction, respectively.

Referring to FIG. 2A and FIG. 2F, a cylindrical proximal connecting member 42 is coaxially connected to the most proximal through piece 31 of the proximal-side bending portion 26. The proximal-side traction wires 37$u$, 37$d$, 37$l$ and 37$r$ are inserted axially movably back and forth through proximal-side coil sheaths 44$u$, 44$d$, 44$l$ and 44$r$ in the flexible tube 24. The distal ends of the proximal-side coil sheaths 44$u$, 44$d$, 44$l$ and 44$r$ are fixed to the internal peripheral surface of the proximal connecting member 42, and form proximal-side sheath fixing portions 47$u$, 47$d$, 47$l$ and 47$r$. The proximal-side sheath fixing portions 47$u$ to 47$r$ are disposed at the same positions in the circumferential direction as the proximal-side wire fixing portions 39$u$ to 39$r$, respectively. That is, the proximal-side sheath fixing portions 47$u$ to 47$r$ for vertical and horizontal bending motions are disposed exactly at the top, bottom, left, and right, respectively.

Referring to FIG. 2A and FIG. 2C, through-holes 51$u$, 51$d$, 51$l$ and 51$r$ are axially formed as through portions through the through piece 31 of the distal-side bending portion 25. The through-holes 51$u$ to 51$r$ are in the shape of long holes having a width slightly greater than the outside diameters of the distal-side traction wires 36$u$ to 36$r$, respectively. The through-holes 51$u$ to 51$r$ respectively extend, in the circumferential direction, fully between the positions of the distal-side wire fixing portions 38$u$ to 38$r$ and the positions of the distal-side sheath fixing portions 46$u$ to 46$r$ that are disposed at positions slightly different from the distal-side wire fixing portions 38$u$ to 38$r$ in one orientation in the circumferential direction. That is, the through-holes 51$u$ to 51$r$ for vertical and horizontal bending motions circumferentially extend from the top to the left in the circumferential direction, from the bottom to the right in the circumferential direction, from the left to the lower side in the circumferential direction, and from the right to the upper side in the circumferential direction, respectively.

The distal-side traction wires 36$u$ to 36$r$ are inserted through the through-holes 51$u$ to 51$r$ from the distal-side wire fixing portions 38$u$ to 38$r$ to the distal-side sheath fixing portions 46$u$ to 46$r$, and extend toward the proximal end in the axial direction in such a manner as to be displaced in one orientation in the circumferential direction. That is, the distal-side traction wires 36$u$ to 36$r$ for vertical and horizontal bending motions extend toward the proximal end in the axial direction in such a manner as to be displaced leftward from the top in the circumferential direction, rightward from the bottom in the circumferential direction, downward from the left in the circumferential direction, and upward from the right in the circumferential direction, respectively. The distal-side traction wires 36$u$ to 36$r$ are supported by the internal peripheral surfaces of the through-holes 51$u$ to 51$r$ axially movably back and forth and circumferentially movably in the through-holes 51$u$ to 51$r$.

Figure 2E:
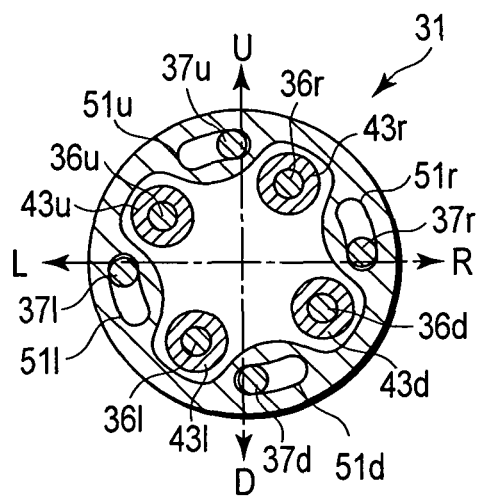
FIG. 2E is a cross-sectional view showing an intermediate portion of the proximal-side bending portion according to the first embodiment of the present invention along the line IIE-IIE of FIG. 2A.

Referring to FIG. 2A and FIG. 2E, through-holes 51$u$, 51$d$, 51$l$ and 51$r$ similar to the through-holes 51$u$ to 51$r$ of the distal-side bending portion 25 are also formed in the through piece 31 of the proximal-side bending portion 26. The proximal-side traction wires 37$u$ to 37$r$ are respectively inserted through the through-holes 51$u$ to 51$r$ from the proximal-side wire fixing portions 39$u$ to 39$r$ to the proximal-side sheath fixing portions 47$u$ to 47$r$ that are disposed at the same positions in the circumferential direction as the proximal-side wire fixing portions 39$u$ to 39$r$, and extend toward the proximal end in the axial direction without being displaced in the circumferential direction. That is, the proximal-side traction wires 37$u$ to 37$r$ for vertical and horizontal bending motions extend toward the proximal end in the axial direction without being displaced from the top, bottom, left, and right in the circumferential direction, respectively. The proximal-side traction wires 37$u$ to 37$r$ are axially movable back and forth in the through-holes 51$u$ to 51$r$, and are supported by the internal peripheral surfaces of the through-holes 51$u$ to 51$r$.

When the proximal-side vertical and horizontal bending operations knobs 29$v$ and 29$h$ are operated, the proximal-side traction wires 37$u$ to 37$r$ for vertical and horizontal bending motions are pulled, and the proximal-side bending portion 26 is bent in the vertical and horizontal directions. Likewise, when the distal-side vertical and horizontal bending operations knobs 28$v$ and 28$h$ are operated, the distal-side traction wires 36$u$ to 36$r$ for vertical and horizontal bending motions are pulled, and the distal-side bending portion 25 is bent in the vertical and horizontal directions.

The endoscope for the two bends according to the present embodiment has the following advantages.

In the endoscope for the two bends according to the present embodiment, the proximal-side wire fixing portions 39$u$ to 39$r$ are disposed at the same positions in the circumferential direction as the distal-side wire fixing portions 38$u$ to 38$r$, respectively. Therefore, the bending orientation of the proximal-side bending portion 26 when the proximal-side traction wires 37u to 37r are pulled exactly corresponds to the bending orientation of the distal-side bending portion 25 when the distal-side traction wires 36u to 36r for vertical and horizontal bending motions in the same orientation are pulled. Consequently, the distal end of the insertion portion 21 can be precisely operated.

Furthermore, in the through piece 31 of the distal-side bending portion 25, the through-holes 51u to 51r respectively extend, in the circumferential direction, fully between the positions of the distal-side wire fixing portions 38u to 38r and the positions of the distal-side sheath fixing portions 46u to 46r that are disposed at positions different from the distal-side wire fixing portions 38u to 38r in one orientation in the circumferential direction. Thus, excessive interference between the distal-side traction wires 36u to 36r and the internal peripheral surfaces of the through-holes 51u to 51r is prevented when the distal-side traction wires 36u to 36r are pulled. Moreover, a common member can be used as many through pieces 31 that constitute the distal-side bending portion 25. This enables the reduction of the manufacturing costs of the endoscope for the two bends.

Although the through pieces integrally formed by, for example, cutting or injection molding including the through-holes are used in the present embodiment, through pieces having wire receptions formed by, for example, soldering a wire reception material to a main body member may be used instead.

A second embodiment of the present invention is described with reference to FIG. 3A to FIG. 8B.

In the distal-side bending portion according to the first embodiment, when the pulling of the traction wires is canceled to return the bending portion from a bent condition to a non-bent neutral condition, a bending skip that causes the bending portion to be bent in the reverse orientation beyond the non-bent neutral condition may occur.

According to the present embodiment, the distal end of an insertion portion can be more precisely operated by preventing the bending skip.

Referring to FIG. 6A and FIG. 6B, in a bending portion 25, regulation pieces 53 as regulation bending members are used as many bending pieces in addition to through pieces 31 similar to those in the first embodiment. In the present embodiment, among 14 bending pieces, the second, fifth, eighth, and eleventh bending pieces from the proximal side serve as the regulation pieces 53, and the other bending pieces serve as the through pieces 31.

Regulation holes 56u, 56d, 56l and 56r are axially formed as regulation through portions through the regulation piece 53. The regulation holes 56u to 56r are in the shape of circular holes having an inside diameter slightly greater than the outside diameters of distal-side traction wires 36u to 36r, respectively. The regulation holes 56u to 56r are disposed, in the circumferential direction, between the positions of distal-side wire fixing portions 38u to 38r and the positions of distal-side sheath fixing portions 46u to 46r that are disposed at positions slightly different from the distal-side wire fixing portions 38u to 38r in one orientation in the circumferential direction. That is, the regulation holes 56u to 56r for vertical and horizontal bending motions are circumferentially disposed on the left side of the top in the circumferential direction, on the right side of the bottom in the circumferential direction, on the lower side of the left in the circumferential direction, and on the upper side of the right in the circumferential direction, respectively. The distal-side traction wires 36u to 36r are inserted through through-holes 51u to 51r of the through pieces 31 and through the regulation holes 56u to 56r of the regulation pieces 53, respectively. In the regulation holes 56u to 56r, the traction wires 36u to 36r are supported by the internal peripheral surfaces of the regulation holes 56u to 56r axially movably back and forth and circumferentially immovably.

In other words, wire fixing portions 38u and 38d for vertical bending motion are respectively disposed on a vertical rotation axis Ov of the bending pieces 31 and 53 that can rotate in the horizontal direction, and sheath fixing portions 46u and 46d for vertical bending motion are respectively disposed on the left and right sides of the vertical rotation axis Ov. Through-holes 51u and 51d for vertical bending motion respectively extend to the left and right from the vertical rotation axis Ov with respect to the bending piece 31. On the other hand, in the regulation piece 53, the regulation holes 56u, 56d for vertical bending motion are respectively disposed on the left and right sides of the vertical rotation axis Ov.

Likewise, the wire fixing portions 38l and 38r for horizontal bending motion are respectively disposed on a horizontal rotation axis Oh of the bending pieces 31 and 53 that can rotate in the vertical direction, and sheath fixing portions 46l and 46d for horizontal bending motion are respectively disposed on the lower side and upper side of the horizontal rotation axis Oh. Through-holes 51l and 51r for horizontal bending motion respectively extend to the lower side and upper side from the horizontal rotation axis Oh with respect to the bending piece 31. On the other hand, in the regulation piece 53, the regulation holes 56l, 56r for horizontal bending motion are respectively disposed on the lower side and upper side of the horizontal rotation axis Oh.

The bending skip in the bending portion according to the first embodiment is described with reference to FIG. 3A to FIG. 5B.

Described below is a leftward bending skip that is caused by the traction wire 36u for upward bending motion when the distal-side bending portion 25 is returned to a non-bent neutral condition from a rightward bent condition.

As shown in FIG. 3A and FIG. 3B, when the bending portion 25 is in the non-bent neutral condition, the traction wire 36u for upward bending motion is disposed on the left side of the vertical rotation axis Ov of the bending pieces 31 capable of rotating in the horizontal direction in the through-hole 51u for vertical bending motion.

As shown in FIG. 4A and FIG. 4B, when the traction wire 36r for rightward bending motion is pulled to bend the bending portion 25 rightward from the non-bent neutral condition, the traction wire 36u for upward bending motion is drawn toward the distal end in the axial direction by the rightward bending motion of the bending portion 25. Sufficiently high axial tension is applied in advance to the traction wires 36u to 36r to enable smooth bending motion. When drawn toward the distal end in the axial direction, the traction wire 36u for upward bending motion is moved rightward in the through-hole 51u for upward bending motion, and comes into contact with the right end wall of the through-hole 51u for upward bending motion. Here, the through-hole 51u for upward bending motion extends up to the vertical rotation axis Ov in the horizontal direction, and the traction wire 36u for upward bending motion is disposed on the vertical rotation axis Ov. In addition, when the traction wire 36u for upward bending motion is drawn toward the distal end in the axial direction, the axial tension applied to the traction wire 36u for upward bending motion is further increased, and the traction wire 36u for upward bending motion is stretched and deformed in the axial direction by elastic deformation.

Furthermore, the pulling of the traction wire 36r for rightward bending motion is canceled to return the bending portion 25 from the rightward bent condition to the non-bent neutral condition. At the same time, the axial tension applied to the traction wire 36u for upward bending motion is rapidly decreased, the traction wire 36u for upward bending motion is rapidly returned and deformed in the axial direction by elastic deformation and is thus rapidly moved leftward from the vertical rotation axis Ov in the through-hole 51u for upward bending motion. Further, the direction of moment acting on the bending portion 25 is rapidly changed from the direction to bend the bending portion 25 rightward to the direction to bend the bending portion 25 leftward.

Figure 5A:
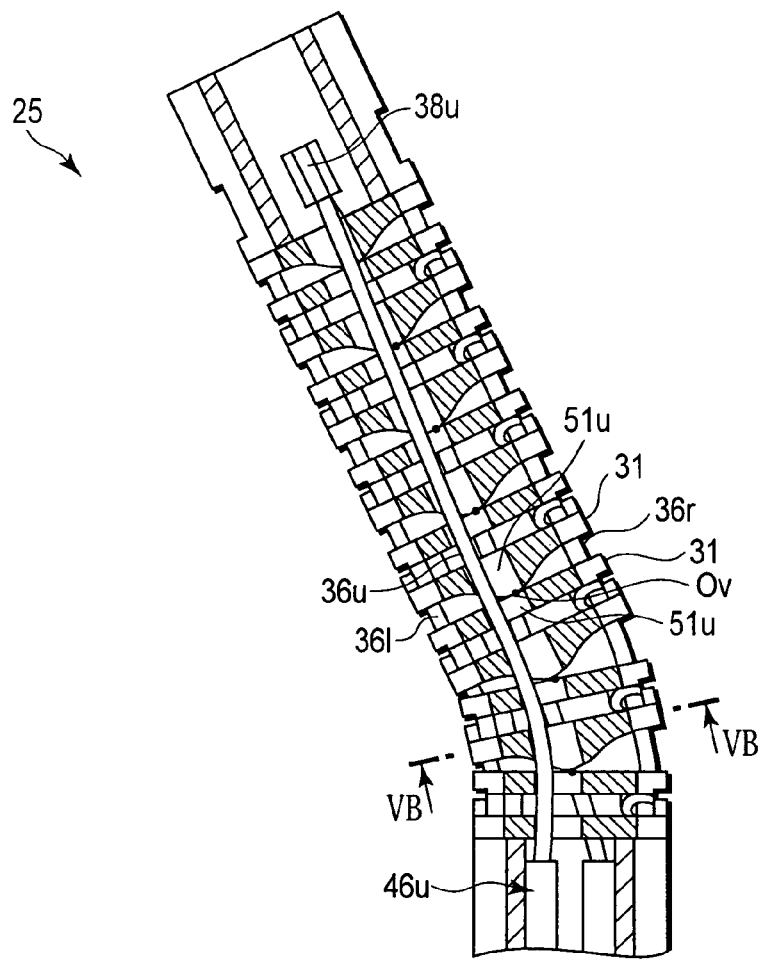
FIG. 5A is a partial longitudinal sectional top view showing the distal-side bending portion according to the first embodiment of the present invention in a leftward bent condition.
Figure 5B:
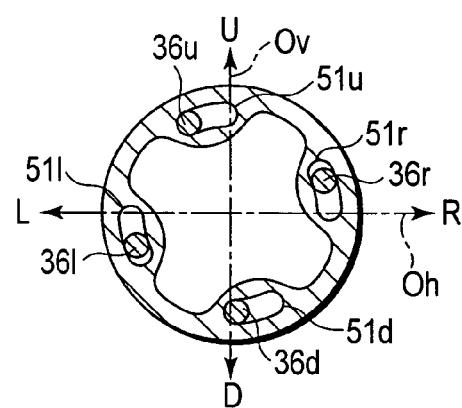
FIG. 5B is a cross-sectional view showing the distal-side bending portion according to the first embodiment of the present invention in the leftward bent condition along the line VB-VB of FIG. 5A.

Consequently, as shown in FIG. 5A and FIG. 5B, the bending skip that causes the bending portion 25 to be bent leftward beyond the non-bent neutral condition may occur.

When the bending portion 25 is returned to the non-bent neutral condition from the leftward bent condition, a rightward bending skip may occur due to the traction wire 36d for downward bending motion. Likewise, when the bending portion 25 is returned to the non-bent neutral condition from the vertically bent condition, a vertical bending skip may occur due to the traction wires 36l and 36r for horizontal bending action. When the bending portion 25 is returned to the non-bent neutral condition from the upward bent condition, a downward bending skip may occur due to the traction wire 36l for leftward bending motion. When the bending portion 25 is returned to the non-bent neutral condition from the downward bent condition, a upward bending skip may occur due to the traction wire 36r for rightward bending motion.

A bending skip preventing function in the bending portion 25 according to the present embodiment is described with reference to FIG. 6A to FIG. 8B.

Described below is the function for preventing a leftward bending skip that may be caused by the traction wire 36u for upward bending action when the distal-side bending portion 25 is returned to a non-bent neutral condition from a rightward bent condition.

Referring to FIG. 6A and FIG. 6B, when the bending portion 25 is in the non-bent neutral condition, the traction wire 36u for upward bending motion is disposed on the left side of the vertical rotation axis Ov of the bending pieces 31 and 53 that can rotate in the horizontal direction.

Figure 7A:
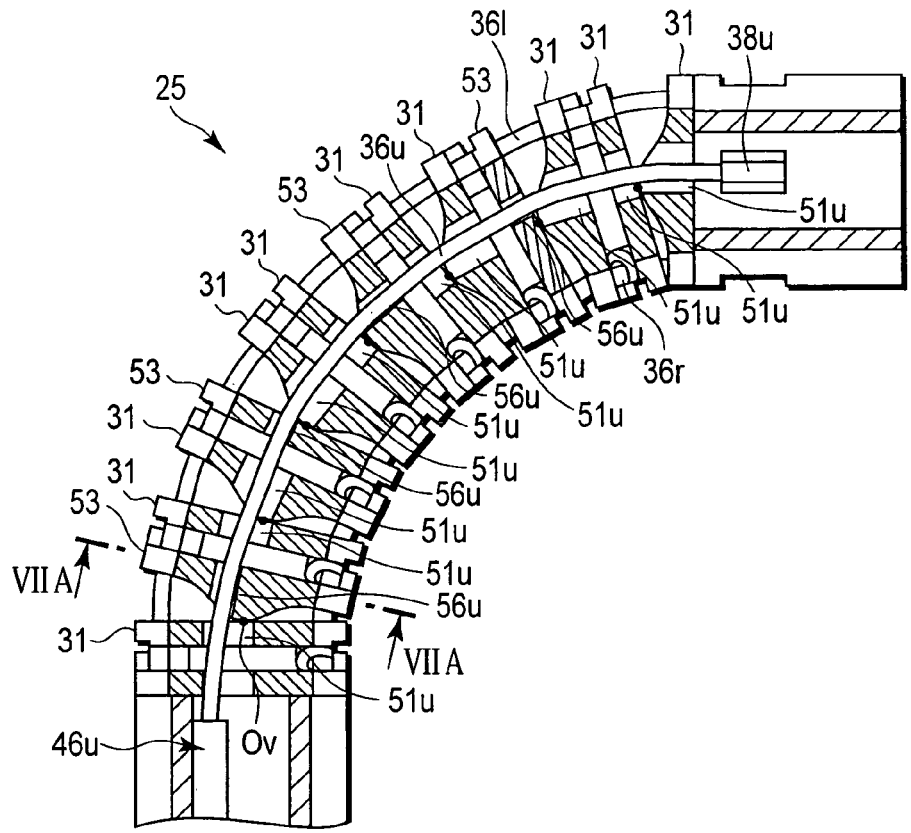
FIG. 7A is a partial longitudinal sectional top view showing the distal-side bending portion according to the second embodiment of the present invention in a rightward bent condition.
Figure 7B:
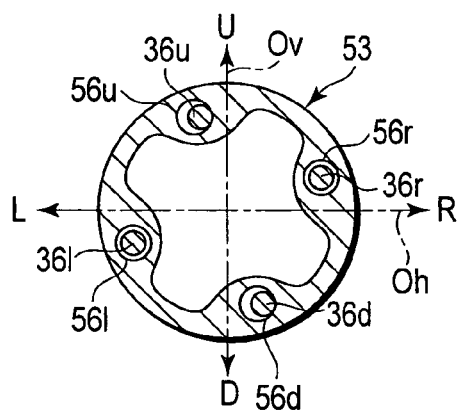
FIG. 7B is a cross-sectional view showing the distal-side bending portion according to the second embodiment of the present invention in the rightward bent condition along the line VIIB-VIIB of FIG. 7A.

Referring to FIG. 7A and FIG. 7B, when the traction wire 36r for rightward bending motion is pulled to bend the bending portion 25 rightward from the non-bent neutral condition, the traction wire 36u for upward bending motion is drawn toward the distal end in the axial direction by the rightward bending action of the bending portion 25. Sufficiently high axial tension is applied in advance to the traction wire 36u for upward bending motion. The through-hole 51u for upward bending action extends up to the vertical rotation axis Ov in the horizontal direction. However, the regulation hole 56u is disposed on the left side of the vertical rotation axis Ov in the horizontal direction. Thus, the rightward movement of the traction wire 36u for upward bending motion is regulated by the regulation hole 56u, and in the through-hole 51u, the traction wire 36u for upward bending action is only slightly moved rightward, and is not moved to the vertical rotation axis Ov and is held on the left side of the vertical rotation axis Ov. The axial tension applied to the traction wire 36u for upward bending motion is further increased by the rightward bending of the bending portion 25, and the traction wire 36u for upward bending motion is stretched and deformed in the axial direction by elastic deformation.

Furthermore, the pulling of the traction wire 36r for rightward bending motion is canceled to return the bending portion 25 from the rightward bent condition to the non-bent neutral condition. At the same time, the axial tension applied to the traction wire 36u for upward bending motion is rapidly decreased, and the traction wire 36u is rapidly returned and deformed in the axial direction by elastic deformation. However, the traction wire 36u is held on the left side of the vertical rotation axis Ov, so that the traction wire 36u for upward bending motion is not rapidly moved leftward. Further, the direction of moment acting on the bending portion 25 is not rapidly changed from the direction to bend the bending portion 25 rightward to the direction to bend the bending portion 25 leftward.

Figure 8A:
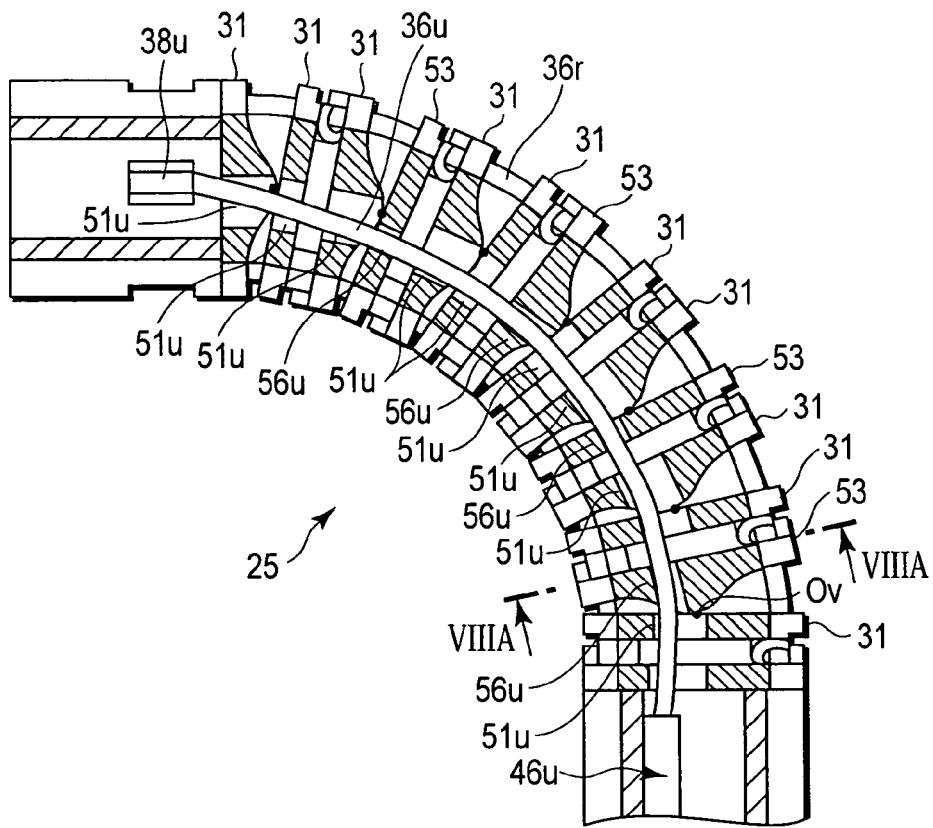
FIG. 8A is a partial longitudinal sectional top view showing the distal-side bending portion according to the second embodiment of the present invention in a leftward bent condition.
Figure 8B:
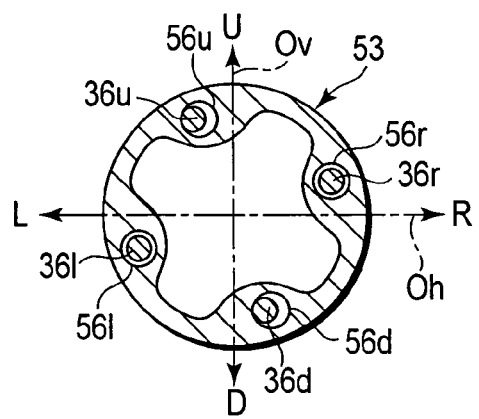
FIG. 8B is a cross-sectional view showing the distal-side bending portion according to the second embodiment of the present invention in the leftward bent condition along the line VIIIB-VIIIB of FIG. 8A.

Consequently, the bending skip shown in FIG. 8A and FIG. 8B that causes the bending portion 25 to be bent leftward beyond the non-bent neutral condition does not occur.

When the curving portion 25 is curved leftward, the traction wire 36d for downward curving motion is held on the right side of the up-and-down direction rotation axis Ov by the regulation hole 56d for downward bending motion. Thus, when the bending portion 25 is returned to the non-bent neutral condition from the leftward bent condition, the rightward bending skip caused by the traction wire 36d for downward bending operation is prevented. When the bending portion 25 is returned to the non-bent neutral condition from the upward curved condition, downward bending skip caused by the traction wire 36l for the leftward bending motion is prevented. When the bending portion 25 is returned to the non-bent neutral condition from the downward curved condition, upward bending skip caused by the traction wire 36r for rightward bending motion is prevented.

The endoscope for the two bends according to the present embodiment has the following advantages.

In the endoscope for the two bends according to the present embodiment, when the bending portion 25 is bent in the right and left orientations, the traction wires 36u and 36d for vertical bending motion are respectively held, by the regulation holes 56u and 56d of the regulation piece 53 for vertical bending motion, on the left and right sides of the vertical rotation axis Ov of the bending pieces 31 and 53 that can rotate in the horizontal direction in the through-holes 51u to 51r for vertical bending motion. Thus, when the bending portion 25 is returned to the non-bent neutral condition from the right and left bent conditions, leftward and rightward bending skips respectively caused by the traction wires 36u and 36d for upward and downward bending actions are prevented. Likewise, when the curving portion 25 is returned to the non-curved neutral condition from the upward and downward curved conditions, downward and upward curving skips respectively caused by the traction wires 36l and 36r for leftward and rightward curving operations are prevented.

A third embodiment of the present invention is described with reference to FIG. 9A to FIG. 9B.

A bending portion 25 according to the present embodiment uses guide pieces 61 as bending pieces. Guide holes 62u, 62d, 62l and 62r are axially formed through the guide piece 61. The guide holes 62u to 62r are in the shape of circular holes having an outside diameter slightly greater than the outside diameters of the traction wires 36u to 36r, respectively. Here, wire fixing portions 38u to 38r are connected to sheath fixing portions 46u to 46r that are disposed at positions slightly different from the wire fixing portions 38u to 38r in one orientation in the circumferential direction, and lines that axially extend in such a manner as to be displaced in the circumferential direction serve as reference lines, respectively. In each guide piece 61, the guide holes 62u to 62r extend along the reference lines, respectively. Thus, excessive interference between the traction wires 36u to 36r and the internal peripheral surfaces of the guide holes 62u to 62r is prevented when the traction wires 36u to 36r are pulled.

As in the second embodiment, the guide holes 62u to 62r for vertical and horizontal bending motions are disposed on the left and right sides of a vertical rotation axis Ov and on the lower side and upper side of a horizontal rotation axis Oh. Thus, when the bending portion 25 is returned to the non-curved neutral condition from the rightward, leftward, upward and down ward bending conditions, leftward rightward, downward and upward bending skips respectively caused by the traction wires 36u to 36r for upward, downward, leftward and rightward bending actions are prevented.

The present invention is applicable to various multi-bendable medical devices in which a plurality of bending portions for bending action are disposed in an insertion portion for insertion into a body. For example, the present invention is not exclusively applicable to a two-bendable medical apparatus, and is also applicable to a multi-bendable medical device having three or more stages in which three or more bending portions are disposed in an insertion portion. Moreover, the present invention is not only applicable to the multi-bends endoscope, but also applicable to a multi-bends treatment instrument configured to treat a living tissue in a body or to a multi-bends over tube configured to assist the insertion of, for example, an endoscope into a body. In particular, the multi-bends treatment instrument has a treatment portion configured to treat a living tissue provided at the distal end of the insertion portion, and therefore requires precise motion of the treatment portion. Thus, the invention of the present application has a considerable advantage in enabling the precise motion of the distal end of the insertion portion. Further, the present invention is not exclusively applied to a manual multi-bends medical apparatus in which bending portions are manually driven, and is also applicable to an electric multi-bends medical apparatus in which bending portions are electrically driven.

In an aspect of the present invention, a medical device for multiple bends, includes an insertion portion which is configured to be inserted into a body and which includes a central axis and is configured to extend in an axial direction of the central axis, wherein: the insertion portion includes:

a distal-side bending portion configured to bend in a bending direction which is substantially orthogonal to the central axis, a proximal-side bending portion which is disposed closer to a proximal side than the distal-side bending portion in the axial direction and which is configured to bend in the bending direction, a distal-side traction member which is inserted through the distal-side bending portion and the proximal-side bending portion and which is disposed on the side of the bending direction, the distal-side traction member including a distal-side fixing portion fixed to the distal end of the distal-side bending portion in the axial direction, the distal-side traction member being pulled toward the proximal end in the axial direction to allow the distal-side bending portion to bend in the bending direction, a proximal-side traction member which is inserted through the proximal-side bending portion and which is disposed on the side of the bending direction, the proximal-side traction member including a proximal-side fixing portion fixed to the distal end of the proximal-side bending portion in the axial direction, the proximal-side traction member being pulled toward the proximal end in the axial direction to allow the proximal-side bending portion to bend in the bending direction, and a holding portion which is provided at the distal end of the proximal-side bending portion in the axial direction and which is disposed on the side of the bending direction and which is configured to hold the distal-side traction member movably back and forth in the axial direction, the proximal-side fixing portion is disposed at substantially the same position as the distal-side fixing portion in a circumferential direction of the central axis, the holding portion is disposed at a position different from the proximal-side fixing portion in the circumferential direction, the distal-side bending portion includes two or more substantially cylindrical bending members which are substantially coaxially arranged in the axial direction and which are rotatably connected to each other, the two or more bending members include at least one through bending member, the through bending member includes a through portion, the through portion being disposed on the side of the bending direction, extending in the axial direction, and supporting the distal-side traction member, the distal-side traction member being inserted through the through portion movably back and forth in the axial direction, and the through portion extends fully between the position of the distal-side fixing portion and the position of the holding portion in the circumferential direction.

In the medical apparatus for the multiple bend according to this aspect, the proximal-side fixing portion of the proximal-side traction member at the distal end of the proximal-side bending portion in the axial direction is disposed at substantially the same position in the circumferential direction as the distal-side fixing portion of the distal-side traction member at the distal end of the distal-side bending portion in the axial direction. Therefore, the bending orientation of the proximal-side bending portion can exactly correspond to the bending orientation of the distal-side bending portion, so that the distal end of the insertion portion can be precisely operated. Here, in the through bending member, the through portion extends fully between the position of the distal-side fixing portion and the position of the holding portion in the circumferential direction. Thus, excessive interference between the distal-side traction member and the through portion is prevented when the distal-side traction member is pulled.

In the aspect of the present invention, in the medical device, the two or more bending members include at least two through bending members.

In the medical device for the multiple bends according to this aspect, a common member can be used as the at least two through bending members that constitute the distal-side bending portion. This enables the reduction of the manufacturing costs of the medical device for the multiple bends.

In an aspect of the present invention, a medical device for multiple bends, includes an insertion portion which is configured to be inserted into a body and which includes a central axis and is configured to extend in an axial direction of the central axis, wherein the inserting portion includes:

a distal-side bending portion configured to bend in a first bending direction and a second bending direction, the first bending direction including a first bending orientation and a third bending orientation which are substantially orthogonal to the central axis and which are opposite to each other, the second bending direction including a second bending orientation and a fourth bending orientation which are substantially orthogonal to the central axis and the first bending direction and which are opposite to each other, a proximal-side bending portion which is disposed closer to a proximal side than the distal-side bending portion in the axial direction and which is configured to bend in the first bending orientation, a first distal-side traction member which is inserted through the distal-side bending portion and the proximal-side bending portion and which is disposed on the side of the first bending orientation, the first distal-side traction member including a first distal-side fixing portion fixed to the distal end of the distal-side bending portion in the axial direction, the first distal-side traction member being pulled toward the proximal end in the axial direction to allow the distal-side bending portion to bend in the first bending orientation, a second distal-side traction member which is inserted through the distal-side bending portion and the proximal-side bending portion and which is disposed on the side of the second bending orientation, the second distal-side traction member including a second distal-side fixing portion fixed to the distal end of the distal-side bending portion in the axial direction, the second distal-side traction member being pulled toward the proximal end in the axial direction to allow the distal-side bending portion to bend in the second bending orientation, a proximal-side traction member which is inserted through the proximal-side bending portion and which is disposed on the side of the bending orientation, the proximal-side traction member including a proximal-side fixing portion fixed to the distal end of the proximal-side bending portion in the axial direction, the proximal-side traction member being pulled toward the proximal end in the axial direction to allow the proximal-side bending portion to bend in the first bending orientation, and a holding portion which is provided at the distal end of the proximal-side bending portion in the axial direction and which is disposed on the side of the bending orientation and which holds the distal-side traction member movably back and forth in the axial direction, the proximal-side fixing portion is disposed at substantially the same position as the first distal-side fixing portion in a circumferential direction of the central axis, the holding portion is disposed on the side of the fourth bending orientation with respect to the proximal-side fixing portion in the circumferential direction, the distal-side bending portion includes three or more substantially cylindrical bending members which are substantially coaxially arranged in the axial direction and which are rotatably connected to each other, the three or more bending members including at least two bending members which are connected to each other rotatably in the first bending direction around a first rotation axis extending in the second bending direction, and at least two bending members which are connected to each other rotatably in the second bending direction around a second rotation axis extending in the first bending direction, the three or more bending members include at least one through bending member, the through bending member includes a through portion which is disposed on the side of the first bending orientation and which is extending in the axial direction, the first distal-side traction member being inserted through the through portion movably back and forth in the axial direction, and the through bending member supporting the first distal-side traction member, the through portion extends fully between the position of the first distal-side fixing portion and the position of the holding portion in the circumferential direction, the three or more bending members include at least one regulation bending member, the regulation bending member includes a regulation through portion which is disposed on the side of the first bending orientation and which is extending in the axial direction, the first distal-side traction member being inserted through the regulation through portion movably back and forth in the axial direction, and the regulation through portion supporting the first distal-side traction member, and the regulation through portion is disposed closer to the side of the fourth bending orientation than the second rotation axis in the second bending direction, and when the second distal-side traction member is pulled toward the proximal end in the axial direction to bend the distal-side bending portion in the second bending orientation, the regulation through portion regulates the movement of the first distal-side traction member to or beyond the second rotation axis in the through portion in the second bending orientation.

In the medical device for the multiple bends according to this aspect, when the regular bending member is not used, in order to pull the second distal-side traction member toward the proximal end in the axial direction to bend the distal-side bending portion in the second bending orientation, tension directed to the distal end in the axial direction is applied to the first distal-side traction member, the first distal-side traction member is moved to or beyond the second rotation axis in the through portion of the through bending member in the second bending orientation, and the first distal-side traction member is stretched and deformed in the axial direction. In order to cancel the pulling of the second distal-side traction member to return the distal-side bending portion from a condition bent in the second bending orientation to a non-bent neutral condition, the first distal-side traction member is rapidly moved in the fourth bending orientation in the through portion by the returning deformation of the first distal-side traction member resulting from the cancellation of the tension applied to the first distal-side traction member, and the direction of rotation moment acting on the distal-side bending portion is rapidly changed from the direction to bend the distal-side bending portion in the second bending orientation to the direction to bend the distal-side bending portion in the fourth bending orientation. This may lead to a bending skip that causes the distal-side bending portion to be rapidly bent in the fourth bending orientation beyond the non-bent neutral condition.

In the medical device for the multiple bends according to this aspect, when the second distal-side traction member is pulled toward the proximal end in the axial direction to bend the distal-side bending portion in the second bending orientation, the regulation through portion of the regulation bending member regulates the movement of the first distal-side traction member to or beyond the second rotation axis in the through portion of the through bending member in the second bending orientation. Therefore, in order to cancel the pulling of the second distal-side traction member to return the distal-side bending portion from the condition bent in the second bending orientation to the non-bent neutral condition, the first distal-side traction member is not rapidly moved in the fourth bending orientation in the through portion by the returning deformation of the first distal-side traction member resulting from the cancellation of the tension applied to the first distal-side traction member, and the direction of rotation moment acting on the distal-side bending portion is not rapidly changed from the direction to bend the distal-side bending portion in the second bending orientation to the direction to bend the distal-side bending portion in the fourth bending orientation. This prevents the bending skip that causes the distal-side bending portion to be rapidly bent in the fourth bending orientation beyond the non-bent neutral condition.

In an aspect of the present invention, a medical device for multiple bends, includes an insertion portion which is configured to be inserted into a body and which includes a central axis and is configured to extend in an axial direction of the central axis, wherein the inserting portion includes:

a distal-side bending portion configured to bend in a bending orientation which is substantially orthogonal to the central axis, a proximal-side bending portion which is disposed closer to a proximal side than the distal-side bending portion in the axial direction and which is configured to bend in the bending orientation, a distal-side traction member which is inserted through the distal-side bending portion and the proximal-side bending portion and which is disposed on the side of the bending orientation, the distal-side traction member including a distal-side fixing portion fixed to the distal end of the distal-side bending portion in the axial direction, the distal-side traction member being pulled toward the proximal end in the axial direction to allow the distal-side bending portion to bend in the bending orientation, a proximal-side traction member which is inserted through the proximal-side bending portion and which is disposed on the side of the bending orientation, the proximal-side traction member including a proximal-side fixing portion fixed to the distal end of the proximal-side bending portion in the axial direction, the proximal-side traction member being pulled toward the proximal end in the axial direction to allow the proximal-side bending portion to bend in the bending orientation, and a holding portion which is provided at the distal end of the proximal-side bending portion in the axial direction and which is disposed on the side of the bending orientation and which is configured to hold the distal-side traction member movably back and forth in the axial direction, the proximal-side fixing portion is disposed at substantially the same position as the distal-side fixing portion in a circumferential direction of the central axis, the holding portion is disposed at a position different from the proximal-side fixing portion in the circumferential direction, the distal-side bending portion includes two or more substantially cylindrical bending members which are substantially coaxially arranged in the axial direction and which are rotationally connected to each other, the two or more bending members includes at least one guide bending member, the guide bending member includes a guide through portion which is disposed on the side of the bending orientation and which is extending in the axial direction, the distal-side traction member being inserted through the guide through portion movably back and forth in the axial direction and the guide through portion supporting the distal-side traction member, and the guide through portion is disposed, in the circumferential direction, on a reference line which connects between the position of the distal-side fixing portion and the position of the holding portion and which is configured to extend in the axial direction in such a manner as to be displaced in the circumferential direction.

In the medical device for the multiple bends according to this aspect, the proximal-side fixing portion of the proximal-side traction member at the distal end of the proximal-side bending portion in the axial direction is disposed at substantially the same position in the circumferential direction as the distal-side fixing portion of the distal-side traction member at the distal end of the distal-side bending portion in the axial direction. Therefore, the bending orientation of the distal-side bending portion can exactly correspond to the bending orientation of the proximal-side bending portion, so that the distal end of the insertion portion can be precisely operated. Here, in the guide bending member, the guide through portion is disposed, in the circumferential direction, on the reference line which connects the position of the distal-side fixing portion to the position of the holding portion and which extends in the axial direction in such a manner as to be displaced in the circumferential direction. Thus, excessive interference between the distal-side traction member and the guide through portion is prevented when the distal-side traction member is pulled.

In the aspect of the present invention, in the medical device, the guide through portion extends along the reference line in the guide bending member.

In the medical device for the multiple bends according to this aspect, the guide through portion extends along the reference line in the guide bending member. Thus, excessive interference between the distal-side traction member and the guide through portion is further prevented when the distal-side traction member is pulled.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical device for multiple bends, the medical device comprising:

an insertion portion which is configured to be inserted into a body and which includes a central axis in an axial direction and is configured to extend in the axial direction of the central axis, wherein:

the insertion portion includes:

a distal-side bending portion configured to bend in a bending direction which is substantially orthogonal to the central axis, a proximal-side bending portion which is disposed closer to a proximal side than the distal-side bending portion in the axial direction and which is configured to bend in the bending direction, a distal-side traction member which is inserted through the distal-side bending portion and the proximal-side bending portion and which is disposed on the side of the bending direction, the distal-side traction member including a distal-side fixing portion fixed to the distal end of the distal-side bending portion in the axial direction, the distal-side traction member being pulled toward the proximal end in the axial direction to allow the distal-side bending portion to bend in the bending direction, a proximal-side traction member which is inserted through the proximal-side bending portion and which is disposed on the side of the bending direction, the proximal-side traction member including a proximal-side fixing portion fixed to the distal end of the proximal-side bending portion in the axial direction, the proximal-side traction member being pulled toward the proximal end in the axial direction to allow the proximal-side bending portion to bend in the bending direction, and a holding portion which is provided at the distal end of the proximal-side bending portion in the axial direction and which is disposed on the side of the bending direction and which is configured to hold the distal-side traction member movably back and forth in the axial direction, the proximal-side fixing portion is disposed at substantially the same position as the distal-side fixing portion in a circumferential direction of the central axis when the distal-side and proximal-side bending portions are unbent, the holding portion is disposed at a position different from the proximal-side fixing portion and the distal-side fixing portion in the circumferential direction of the central axis, and is configured to extend the distal-side traction member in an oblique direction relative to the central axis when the distal-side and proximal-side bending portions are unbent, the distal-side bending portion includes two or more substantially cylindrical bending members which are substantially coaxially arranged in the axial direction and which are rotatably connected to each other, the two or more bending members include at least one through bending member, the through bending member includes a through portion, the through portion being disposed on the side of the bending direction, extending in the axial direction, and supporting the distal-side traction member, the distal-side traction member being inserted through the through portion movably back and forth in the axial direction, and the through portion extends fully between the position of the distal-side fixing portion and the position of the holding portion in the circumferential direction.

2. The medical device for the multiple bend according to claim 1, wherein the two or more bending members include at least two through bending members.

3. A medical device for multiple bends, the medical device comprising:

an insertion portion which is configured to be inserted into a body and which includes a central axis in an axial direction and is configured to extend in the axial direction of the central axis, wherein:

the insertion portion includes:

a distal-side bending portion configured to bend in a first bending direction and a second bending direction, the first bending direction including a first bending orientation and a third bending orientation which are substantially orthogonal to the central axis and which are opposite to each other, the second bending direction including a second bending orientation and a fourth bending orientation which are substantially orthogonal to the central axis and the first bending direction and which are opposite to each other, a proximal-side bending portion which is disposed closer to a proximal side than the distal-side bending portion in the axial direction and which is configured to bend in the first bending orientation, a first distal-side traction member which is inserted through the distal-side bending portion and the proximal-side bending portion and which is disposed on the side of the first bending orientation, the first distal-side traction member including a first distal-side fixing portion fixed to the distal end of the distal-side bending portion in the axial direction, the first distal-side traction member being pulled toward the proximal end in the axial direction to allow the distal-side bending portion to bend in the first bending orientation, a second distal-side traction member which is inserted through the distal-side bending portion and the proximal-side bending portion and which is disposed on the side of the second bending orientation, the second distal-side traction member including a second distal-side fixing portion fixed to the distal end of the distal-side bending portion in the axial direction, the second distal-side traction member being pulled toward the proximal end in the axial direction to allow the distal-side bending portion to bend in the second bending orientation, a proximal-side traction member which is inserted through the proximal-side bending portion and which is disposed on the side of the bending orientation, the proximal-side traction member including a proximal-side fixing portion fixed to the distal end of the proximal-side bending portion in the axial direction, the proximal-side traction member being pulled toward the proximal end in the axial direction to allow the proximal-side bending portion to bend in the first bending orientation, and a holding portion which is provided at the distal end of the proximal-side bending portion in the axial direction and which is disposed on the side of the bending orientation and which holds the distal-side traction member movably back and forth in the axial direction, the proximal-side fixing portion is disposed at substantially the same position as the first distal-side fixing portion in a circumferential direction of the central axis when the distal-side and proximal-side bending portions are unbent, the holding portion is disposed on the side of the fourth bending orientation with respect to the proximal-side fixing portion in the circumferential direction the holding portion is configured to extend the distal-side traction member in an oblique direction relative to the central axis when the distal-side and proximal-side bending portions are unbent, the distal-side bending portion includes three or more substantially cylindrical bending members which are substantially coaxially arranged in the axial direction and which are rotatably connected to each other, the three or more bending members including at least two bending members which are connected to each other rotatably in the first bending direction around a first rotation axis extending in the second bending direction, and at least two bending members which are connected to each other rotatably in the second bending direction around a second rotation axis extending in the first bending direction, the three or more bending members include at least one through bending member, the through bending member includes a through portion which is disposed on the side of the first bending orientation and which is extending in the axial direction, the first distal-side traction member being inserted through the through portion movably back and forth in the axial direction, and the through bending member supporting the first distal-side traction member, the through portion extends fully between the position of the first distal-side fixing portion and the position of the holding portion in the circumferential direction, the three or more bending members include at least one regulation bending member, the regulation bending member includes a regulation through portion which is disposed on the side of the first bending orientation and which is extending in the axial direction, the first distal-side traction member being inserted through the regulation through portion movably back and forth in the axial direction, and the regulation through portion supporting the first distal-side traction member, and the regulation through portion is disposed closer to the side of the fourth bending orientation than the second rotation axis in the second bending direction, and when the second distal-side traction member is pulled toward the proximal end in the axial direction to bend the distal-side bending portion in the second bending orientation, the regulation through portion regulates the movement of the first distal-side traction member to or beyond the second rotation axis in the through portion in the second bending orientation.

4. A medical device for multiple bends, the medical device comprising:

an insertion portion which is configured to be inserted into a body and which includes a central axis in an axial direction and is configured to extend in the axial direction of the central axis, wherein:

the insertion portion includes:

a distal-side bending portion configured to bend in a bending orientation which is substantially orthogonal to the central axis, a proximal-side bending portion which is disposed closer to a proximal side than the distal-side bending portion in the axial direction and which is configured to bend in the bending orientation, a distal-side traction member which is inserted through the distal-side bending portion and the proximal-side bending portion and which is disposed on the side of the bending orientation, the distal-side traction member including a distal-side fixing portion fixed to the distal end of the distal-side bending portion in the axial direction, the distal-side traction member being pulled toward the proximal end in the axial direction to allow the distal-side bending portion to bend in the bending orientation, a proximal-side traction member which is inserted through the proximal-side bending portion and which is disposed on the side of the bending orientation, the proximal-side traction member including a proximal-side fixing portion fixed to the distal end of the proximal-side bending portion in the axial direction, the proximal-side traction member being pulled toward the proximal end in the axial direction to allow the proximal-side bending portion to bend in the bending orientation, and a holding portion which is provided at the distal end of the proximal-side bending portion in the axial direction and which is disposed on the side of the bending orientation and which is configured to hold the distal-side traction member movably back and forth in the axial direction, the proximal-side fixing portion is disposed at substantially the same position as the distal-side fixing portion in a circumferential direction of the central axis when the distal-side and proximal-side bending portions are unbent, the holding portion is disposed at a position different from the proximal-side fixing portion and the distal-side fixing portion in the circumferential direction, the holding portion is configured to extend the distal-side traction member in an oblique direction relative to the central axis when the distal-side and proximal-side bending portions are unbent, the distal-side bending portion includes two or more substantially cylindrical bending members which are substantially coaxially arranged in the axial direction and which are rotationally connected to each other, and at least a pair of one bending member and the other bending member out of the two or more bending members on the side of the bending direction is arranged with:

a first through hole which is configured to pass through the one bending member so as to be able to move the distal-side traction member back and forth, and which is configured to pass through a reference line, which connects the position of the distal-side fixing portion and the position of the holding portion and which extends in the axial direction in such a manner as to be displaced in the circumferential direction with respect to the side of the bending direction; and a second through hole which is configured to pass through the other bending member so as to be able to move the distal-side traction member back and forth and which is configured to pass through the reference line at a position which is displaced in the circumferential direction with respect to the one bending member.

* * * * *